United States Patent
Suzuki

(10) Patent No.: US 7,371,873 B2
(45) Date of Patent: May 13, 2008

(54) SULFOXYALKYLTHIOPHENE AND PROCESS FOR PRODUCING THE SAME

(75) Inventor: Hideo Suzuki, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 64 days.

(21) Appl. No.: 10/580,864

(22) PCT Filed: Nov. 17, 2004

(86) PCT No.: PCT/JP2004/017063

§ 371 (c)(1),
(2), (4) Date: May 26, 2006

(87) PCT Pub. No.: WO2005/056545

PCT Pub. Date: Jun. 23, 2005

(65) Prior Publication Data

US 2007/0260071 A1    Nov. 8, 2007

(30) Foreign Application Priority Data

Dec. 10, 2003 (JP) ............................. 2003-411124

(51) Int. Cl.
*C07D 333/16* (2006.01)
(52) U.S. Cl. ....................................................... 549/78
(58) Field of Classification Search .................. 549/78
See application file for complete search history.

(56) References Cited

FOREIGN PATENT DOCUMENTS

WO    WO-01/19809 A1    3/2001

OTHER PUBLICATIONS

Morison et al., Org. Chem. 3rd Ed. (1973), pp. 256.*
March, Adv. Org. Chem. 2nd Ed. (1977), pp. 708-709.*
Cornelus G.M. Janssen et al., the Synthises of bis(4-methyl-3-pentenyl)thiopenes, Recueil, Journal of Royal Netherlands Chemical Society, Jul.-Aug. 1979, pp. 448-451, vol. 98/7-8.

Y. Ikenoue et al., Electrochemical Studies of Self-Doped Conducting Polymers: Verification of the 'Cation-Popping' Doping Mechanism, Synthetic Metals, 1989, pp. 305-319, vol. 30.
Peter Bäuerle, End-Capped Oligothiophenes—New Model Compounds for Polythiophenes, Advanced Materials, 1992, vol. 4-2. pp. 102-107.
Thomas X. Neenan et al., Synthesis of High Carbon Materials form Acetylenic Precursors, Preparation of Aromatic Monomers Bearing Multiple Ehtynyl Groups, Journal of Organic Chemistry, 1988, pp. 2489-2496, vol. 53.
Marie Angelopoulos, Conducting Polymers in Microelectronics, Handbook of Coducting Polymers, 1998, p. 930, 2nd ed.
A.O. Patil et al., Water-Soluble Conducting Polymers, Journal of the American Chemical Society, 1987, pp. 1858-1859, vol. 109.

* cited by examiner

*Primary Examiner*—Taofiq Solola
(74) *Attorney, Agent, or Firm*—Birch, Stewart, Kolasch & Birch, LLP

(57) ABSTRACT

A sulfoalkylthiophene compound of the following formula [1] and a hydroxyalkylthiophene compound of the following formula [2], from which a useful π-conjugated conductive polymer monomer capable of oxidation polymerization can be provided:

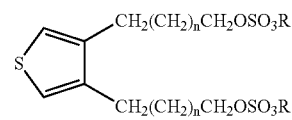

[1]

(wherein R is a hydrogen atom, an alkali metal atom or an alkaline earth metal atom, and n is an integer of 1 to 3)

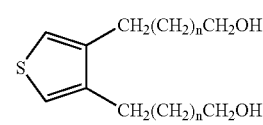

[2]

(wherein n is as defined above).

7 Claims, No Drawings

SULFOXYALKYLTHIOPHENE AND PROCESS FOR PRODUCING THE SAME

TECHNICAL FIELD

The present invention relates to a monomer for a π-conjugated conducting polymer and, more particularly, to sulfoxyalkylthiophene and a process for production thereof.

BACKGROUND ART

There have been known many species of π-conjugated conducting polymer having sulfonic acid groups. One of them is polythiophene capable of self-doping, which is commonly applied to electron beam lithography. (See Non-Patent Documents 1 and 2.)

In addition, among known species of water-soluble self-doping polythiophene for antistatic use are poly(3-thiophene-β-butanesulfonate) and poly(3-thiophene-β-ethanesulfonate), (See Non-Patent Documents 1 and 3.)

However, nothing has been reported about the sulfoxyalkylthiophene disclosed in the present invention.

Incidentally, among known species of hydroxyalkynylthiophene is 3-[4-(3-hydroxy-prop-1-ynyl)-thiophen-3-yl]-prop-2-yn-1-ol (3,4HTPO), which is represented by formula [7] below. (See Patent Document 1.)

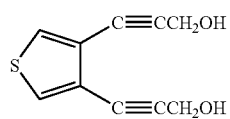

Patent Document 1: WO Publication No. WO01/19809 (pages, 21, 27, and 41 to 42)

Non-Patent Document 1: "Synth. Met." Elsevier Sequoia (Netherlands), 1989, vol. 30, p. 305 to 319

Non-Patent Document 2: "Handbook of Conducting Polymers" 2nd ed. Revised and enlarged, Marcel Dekkers Inc. (USA), 1998, p. 930

Non-Patent Document 3: "J. Amer. Chem. Soc." American Chemical Society (USA), 1987, vol. 109, p. 1858 to 1859

DISCLOSURE OF INVENTION

Problems to be Solved by the Invention

It is an object of the present invention to provide a new species of sulfoxyalkylthiophene as a monomer capable of oxidative polymerization to give a π-conjugated conducting polymer. It is another object of the present invention to provide a process for production of said compound.

Means for Solving the Problems

In order to achieve the above-mentioned object, the present inventor carried out a series of researches which led to the finding that a species of alkylthiophene represented by the formula [1] or [2] below is a monomer capable of oxidative polymerization to give a π-conjugated conducting polymer. The present invention was completed on the basis of this finding.

The present invention covers any of the following.

(1) 3,4-bis(1-sulfoxyalkyl)thiophene represented by formula [1] below.

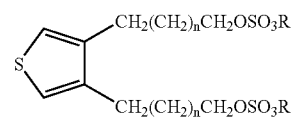

(where R denotes a hydrogen atom, alkali metal atom, or alkaline earth metal atom, and n denotes an integer of 1 to 3.)

(2) 3,4-bis(1-hydroxyalkyl)thiophene represented by formula [2] below.

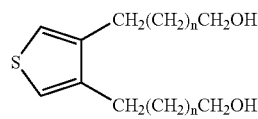

(where n denotes an integer of 1 to 3.)

(3) 3,4-bis(1-sulfoxypropyl-3-yl)thiophene represented by formula [3] below.

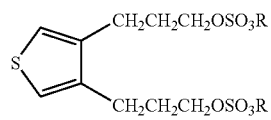

(where R denotes a hydrogen atom, alkali metal atom, or alkaline earth metal atom.)

(4) 3,4-bis(1-hydroxypropyl-3-yl)thiophene represented by formula [4] below.

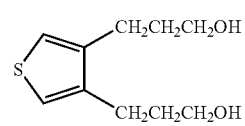

(5) Sulfoxyalkynylthiophene defined in (1) or (3) above wherein the alkali metal atom is sodium or potassium.

(6) A process which comprises steps of reacting 3,4-bis(1-hydroxyalkyl)thiophene represented by formula [2] below

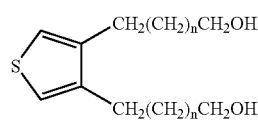

(where n denotes an integer of 1 to 3.)

with a sulfur trioxide compound to give 3,4-bis(1-sulfoxyalkyl)thiophene represented by the formula [5] below.

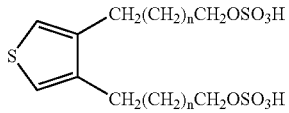
[5]

(where n is defined as above.)

and reacting it with an alkali metal compound or alkaline earth metal compound to give a metal salt of 3,4-bis(1-sulfoxyalkyl)thiophene represented by formula [6] below.

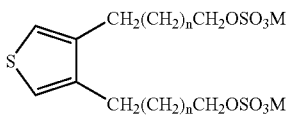
[6]

(where M denotes alkali metal atom or alkaline metal atom, and n is defined as above.)

(7) A process which comprises a step of reducing 3-[4-(3-hydroxy-prop-1-ynyl)-thiophen-3-yl]-prop-2-yn-1-ol (3,4-HTPO for short hereinafter) represented by formula [7] below

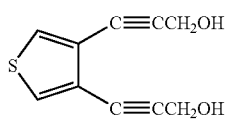
[7]

to give 3,4-bis(1-hydroxy-propyl-3-yl)thiophene (3,4-BHT for short hereinafter) represented by formula [4] below.

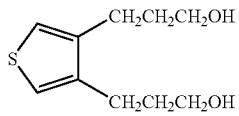
[4]

(8) The process for producing a metal salt of sulfoxyalkynylthiophene as defined in (6) above, wherein the alkali metal atom is sodium or potassium.

(9) The process for producing a metal salt of sulfoxyalkynylthiophene as defined in (6) above, wherein the sulfur trioxide compound is sulfur trioxide, sulfur trioxide-1,4-dioxane complex, sulfur trioxide-DMF (N,N-dimethylformamide) complex, or sulfur trioxide-pyridine complex.

EFFECT OF THE INVENTION

The present invention provides a new species of sulfoxyalkylthiophene as a monomer capable of oxidative polymerization to give a π-conjugated conducting polymer.

BEST MODE FOR CARRYING OUT THE INVENTION

A detailed description of the present invention will be given below.

Formula [1] that represents the compound according to the present invention has an integer of 1 to 3 for n; however, the value of n should preferably be 1. In this case, formula [1] is equivalent to formula [3].

Formula [2] that represents the compound according to the present invention has an integer of 1 to 3 for n; however, the value of n should preferably be 1. In this case, formula [2] is equivalent to formula [4].

Formula [6] that represents a metal salt of sulfoxyalkynylthiophene has an integer of 1 to 3 for n; however, the value of n should preferably be 1.

The following description is based on the assumption that the foregoing formulas [1], [2], [5], and [6] have an integer of 1 for n. The compound according to the present invention is produced by the reaction shown by the following schemes.

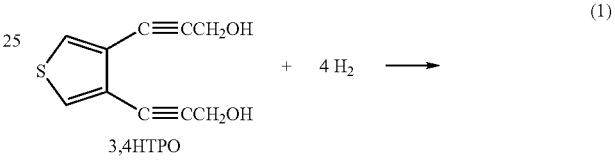
(1)

(2)

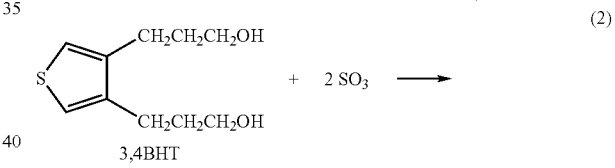

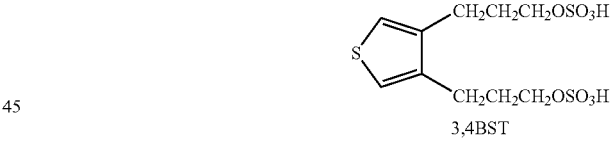
(3)

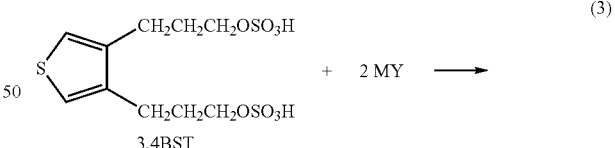

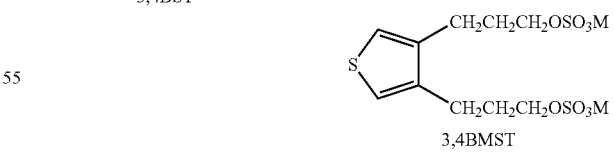

(In the third scheme above, M denotes an alkali metal atom or alkaline earth metal atom, and Y denotes a residue.)

The foregoing three schemes will be described sequentially.

The starting material (3,4-HTPO) is produced by the reaction which is represented by the following schemes mentioned in WO Publication No. 01/19809.

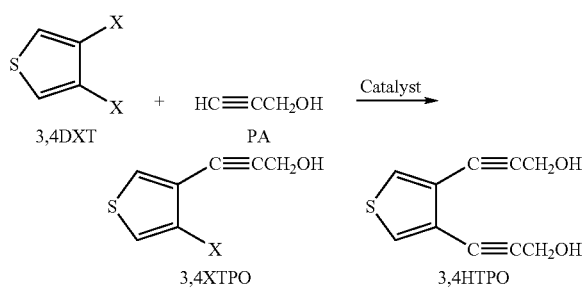

(where X is defined as above.)

The starting material, or 3,4-dihalogenothiophene (3,4-DXT) includes 3,4-difluorothiophene, 3,4-dichlorothiophene, 3,4-dibromothiophene, and 3,4-diuodothiophene, with the third one being preferable from the standpoint of reactivity and economy. The second starting material, or propargyl alcohol may be a commercial one.

The reaction uses a catalyst, which is a combination of $Pd(Ph_3P)_4$ (2+1 mol %) and CuI (3+1.5 mol %), and a solvent, which is n-propylamine. After heating with refluxing, the reaction product is purified by silica gel column chromatography. Thus there is obtained 3,4-HTPO as desired.

Incidentally, although WO Publication No. 01/19809 mentions nothing about the intermediate product or 3,4-XTPO, the present inventors found that the reaction product contains 3-(4-halogeno-thiophen-3-yl)-prop-2-yn-1-ol (3,4-XTPO) in addition to 3,4-HTPO. This intermediate product was separated and analyzed by purifying the reaction product by silica gel column chromatography.

The first step of the reaction is reduction of 3,4-HTPO (represented by formula [7] above) into 3,4-BHT (represented by formula [4] above). This reduction reaction is accomplished by any known process for conversion of the triple bond into the single bond. Some examples of the process include (1) reduction by a metal or metal salt, (2) reduction by a metal hydride, (3) reduction by a metal hydride complex, (4) reduction by diborane and substituted borane, (5) reduction by hydrazine, (6) reduction by diimide, (7) reduction by a phosphorus compound, (8) electrolytic reduction, and (9) catalytic reduction.

Of these processes, catalytic reduction is most practical. The catalytic reduction used in the present invention is as follows. The catalyst metal is selected from palladium, ruthenium, rhodium, platinum, nickel, cobalt, and iron (which belong to Group 8 of the periodic table) and copper (which belongs to Group 1 of the periodic table). They may be used alone or in combination with other elements. They may be used in the form of metal, Raney catalyst, or complex, or they may be supported on a carrier such as diatomaceous earth, alumina, zeolite, and carbon.

Typical examples of the catalyst include palladium-carbon, ruthenium-carbon, rhodium-carbon, platinum-carbon, palladium-alumina, ruthenium-alumina, rhodium-alumina, platinum-alumina, reduced nickel, reduced cobalt, Raney nickel, Raney cobalt, Raney copper, copper oxide, copper chromate, chlorotris(triphenylphosphine)rhodium, chlorohydridetris(triphenylphosphine)ruthenium, dichlorotris(triphenylphosphine)ruthenium, and hydridecarbonayl(triphenylphosphine)iridium. Of these examples, palladium-carbon and ruthenium-carbon are most desirable.

The amount of the catalyst (in terms of 5% supported catalyst) should preferably be 0.1 to 30 wt % (particularly 0.5 to 20 wt %) for the starting material. The solvent may be selected from alcohols (such as methanol, ethanol, and propanol), ethers (such as dioxane, tetrahydrofuran, and dimethoxyethane), and esters (such as ethyl acetate and propyl acetate).

The amount of the solvent should preferably be 1 to 50 times by weight, particularly 3 to 10 times by weight, the amount of the raw material. The pressure of hydrogen should preferably be in the range of normal pressure to 10 MPa (100 kg/cm$^2$), particularly from normal pressure to 5 MPa (50 kg/cm$^2$). The reaction temperature should preferably be in the range of 0 to 180° C., particularly 10 to 150° C.

It is possible to trace the reaction by determining the amount of hydrogen absorbed. The theoretical amount of hydrogen absorption can be determined by analyzing the sample by gas chromatography after hydrogen absorption. The reaction may be accomplished batchwise or continuously. The reaction may be followed by removal of catalyst by filtration, concentration, and purification by recrystallization or column chromatography.

The next step of reaction is sulfonation of 3,4-BHT into 3,4-BST. The sulfonating agent for this step is sulfur trioxide compound, which includes not only sulfur trioxide proper but also complex of sulfur trioxide with N,N-dimethylformamide (DMF), 1,4-dioxane, or pyridine. The amount of the sulfonating agent is 1 to 1.5 mol equivalent for the amount of hydroxyl groups in the raw material.

The solvent may be selected from amide compounds, such as N,N-dimethylformamide (DMF), N,N-dimethylacetamide (DMAc), N-methylpyrrolidone (NMP), and 1,3-dimethyl-2-imidazolidinone (DMI), and ether compounds, such as tetrahydrofuran (THF), 1,2-dimethoxyethane, and 1,4-dioxane. Of these solvents, DMF and DMAc are preferable. The amount of the solvent should preferably be 1 to 10 times by weight (particularly 2 to 5 times by weight) the amount of the starting material.

The reaction temperature should preferably be 0 to 150° C., particularly 10 to 100° C. The reaction time should preferably be 1 to 5 hours; it may be determined from the result of analysis of the reaction liquid by liquid chromatography.

After the reaction is complete, the reaction liquid is distilled for concentration and solvent removal. The residue is dissolved in acetone with heating, and the resulting solution is hold to stand at room temperature for crystallization. The crystals are filtered off and dried. Thus there is obtained 3,4-bis(1-sulfoxypropyl)thiophene (3,4-BST) as the desired product.

The scheme (3) is intended to react 3,4-BST with a metal compound to give a metal salt of sulfoxypropylthiophene. This reaction proceeds in the following manner.

The metal compound includes alkali metal compounds and alkaline earth metal compounds, such as hydroxides, carbonates, and organic salts of lithium, sodium, potassium, rubidium, cesium, magnesium, calcium, strontium, and barium.

Their typical examples are sodium hydroxide, potassium hydroxide, magnesium hydroxide, calcium hydroxide, sodium carbonate, potassium carbonate, magnesium carbonate, calcium carbonate, sodium hydrogen carbonate, potassium hydrogen carbonate, magnesium hydrogen carbonate, calcium hydrogen carbonate, sodium formate, potassium formate, magnesium formate, calcium formate, sodium acetate, potassium acetate, magnesium acetate, and calcium acetate.

Of these metal compounds, preferable ones are sodium hydroxide, potassium hydroxide, magnesium hydroxide, calcium hydroxide, sodium carbonate, potassium carbonate, magnesium carbonate, calcium carbonate, sodium hydrogen carbonate, and potassium hydrogen carbonate.

The amount of the metal compound should preferably be 1 to 2 mol equivalent, particularly 1 to 1.5 mol equivalent, for the amount of sulfonic groups in the starting material.

The solvent includes not only water (which dissolves the raw material and the metal compound) but also imide compounds, such as N,N-dimethylformamide (DMF), N,N-dimethylacetamide (DMAc), N-methylpyrrolidone, and 1,3-dimethyl-2-imidazolidinone (DMI), which may be used alone or in combination with water. The amount of the solvent should preferably be 1 to 10 times by weight, particularly 2 to 5 times by weight, the amount of the starting material.

The reaction temperature should preferably be −20 to 50° C., particularly 0 to 40° C. The reaction time should preferably be 0.5 to 5 hours; it may be determined from the result of analysis of the reaction liquid by liquid chromatography.

After the reaction is complete, the reaction liquid is distilled for concentration and solvent removal. The residue is dissolved in methanol to remove the excess metal compound. After concentration, the residue is dissolved in ethanol and the resulting solution is allowed to stand for crystallization. Thus there is obtained a metal salt of 3,4-bis(1-sulfoxyalkyl)thiophene (3,4-BSST if the metal is sodium).

Incidentally, the reaction solution obtained by sulfonation according to the scheme (2) may be used as such for the reaction with the metal salt according to the scheme (3).

The above-mentioned reaction and purification may be accomplished batchwise or continuously and under atmospheric pressure or adequate pressure.

EXAMPLES

The invention will be described in more detail with reference to the following Examples, which are not intended to restrict the scope thereof. Incidentally, the analytical methods employed in the examples are listed below.
(1) Gas chromatography (GC)
   Instrument: Shimadzu GC-17A
   Column: capillary column, CBP1-W25-100 (25 m×0.53 mmφ×1 μm)
   Column temperature: 100° C. (hold for 2 min), 8° C./min (rate of temperature rise), 290° C. (hold for 10 min).
   Injection temperature: 290° C.
   Detector temperature: 290° C.
   Carrier gas: helium
   Method for detection: by FID
(2) Mass spectrometry (MASS)
   Instrument: LX-1000 (JEOL Ltd.)
   Method for detection: by FAB
(3) $^1$H NMR
   Instrument: INOVA 500 (VARIAN Corp.)
   Solvent: CDCl$_3$
   Standard reference material: tetramethylsilane (TMS)
(4) $^{13}$C NMR
   Instrument: INOVA 500 (VARIAN Corp.)
   Solvent: CDCl$_3$
   Standard reference material: CDCl$_3$ (δ: 77.1 ppm)

(5) Melting point (mp.)
   Instrument: MP-J3 (from Kiki Yanako)
(6) Liquid chromatography (LC)
   Instrument: Shimadzu LC-10A
   Column: YMC-Pack ODS-AM (S-5 μm, 120A, AM-303, AM12S05-2546WT) (250 mm×4.6 mmφ)
   Column temperature: 40° C.
   Detector wavelength: UV 230 nm
   Eluent: H$_2$O/CH$_3$CN=½,
   Flow rate: 0.5 mL/min Referential Example 1

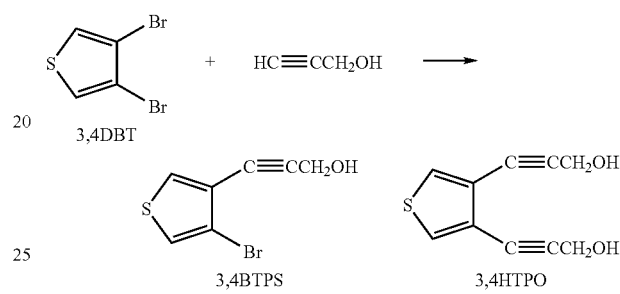

3,4DBT 3,4BTPS 3,4HTPO

A 300-mL four-neck flask was charged with 25.0 g (103 mmol) of 3,4-dibromothiophene (3,4-DBT) and 100 g of n-propylamine. With stirring at 25° C., the flask was further charged with 2.38 g (2.06 mmol) of tetrakistriphenylphosphine palladium and 0.588 g (3.09 mmol) of copper iodide. The flask was charged 17.3 g (309 mmol) of propargyl alcohol by drops over 10 minutes. Stirring was continued for 1 hour at 25° C. and then for 7 hours at 54° C. in an oil bath at 70° C.

The flask was further charged with 1.19 g (1.03 mmol) of tetrakistriphenylphosphine palladium and 0.29 g (1.10 mmol) of copper iodide. The flask was given 8.7 g (155 mmol) of propargyl alcohol dropwise. The reactants were stirred for 20 hours at 57° C. in an oil bath at 70° C.

After the reaction was complete, the reaction liquid was concentrated and the residue was dissolved in ethyl acetate and water. Insoluble matter was removed by filtration with the help of Celite. The organic layer was separated and concentrated to give 37.5 g of oily substance. The oily substance was analyzed by gas chromatography. The result of analysis gave a new peak A (40.8 area %) and a new peak B (23.3 area %). The oily substance was purified by column chromatography with 140 g of silica gel (eluent:ethyl acetate/n-heptane=1:9-1:5). There was obtained 16.0 g of oily substance (as fraction 1), with 70.6% purity, in a 57% yield. There was also obtained 4.56 g of oily substance (as fraction 2), with 76.5% purity, in a 23.7% yield.

The thus obtained oily substance (as fraction 1) with 70.6% purity in an amount of 16.0 g was further purified by column chromatography with 140 g of silica gel (eluent: ethyl acetate/n-heptane=1:9-1:5). There was obtained 10.3 g of oily substance (as fraction 6), with 93.0% purity, in 84.7% recovery. This oily substance was identified as 3-(4-bromothiophen-3-yl)-prop-2-yn-1-ol (3,4-BTPO) by the following analytical data.

$^1$H NMR (CDCl$_3$, δ ppm): 4.43 (s, 2H), 7.13 (d, J=3.36 Hz, 1H), 7.36 (d, J=3.67 Hz, 1H) $^{13}$C NMR (CDCl$_3$, δ ppm): 51.2564, 78.5646, 90.6355, 113.3275, 123.8113, 122.9033, 127.1915.

On the other hand, the oily substance (as fraction 2) with 76.5% purity in an amount of 4.56 g was purified again by column chromatography with 40 g of silica gel (eluent:ethyl acetate/n-heptane=1:9-1:5). There was obtained 1.0 g of oily substance (from fraction 1), with 90.6% purity. This oily substance was identified as 3-[4-(3-hydroxy-prop-1-ynyl)-thiophen-3-yl]-prop-2-yn-1-ol (3,4-HTPO) by the following analytical data.

MASS (FAB$^+$, m/e (%)): 191([M-H]$^+$, 3), 174(29), 146 (62), 102(100). $^1$H NMR (CDCl$_3$, δ ppm): 4.45 (s, 4H), 7.31 (s, 2H) $^{13}$C NMR (CDCl$_3$, δ ppm): 50.9736 (2C), 78.9914 (2C), 89.8720 (2C), 124.0855 (2C), 128.3813 (2C).

Example 1

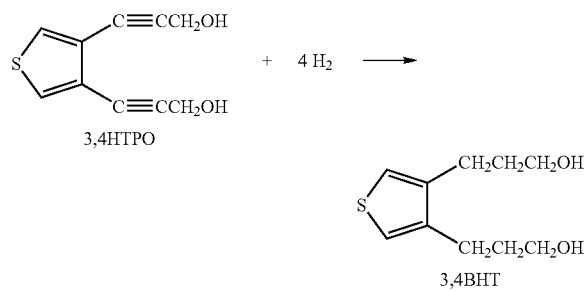

A 100-mL hastelloy autoclave was charged with 19.2 g (0.10 mmol) of 3,4-HTPO, 1.95 g (5 wt %) of 5% Pd/C (containing 50.7% water), and 100 g of ethanol. The atmosphere in the autoclave was replaced by nitrogen. Stirring was started at a hydrogen initial pressure of 5 MPa. The reaction temperature was raised with stirring. Reaction was continued at 120° C. for 6 hours. After cooling to room temperature, the catalyst was removed by filtration, and the reaction product was concentrated and dried. There was obtained 20.0 g (0.10 mmol) of crystals (which solidify at room temperature) composed mainly of a single component (in a 100% yield). This product was found by gas chromatography to be different from the raw material.

The resulting product was identified as 3,4-bis(1-hydroxypropyl-3-yl)thiophene (3,4-BHT) by the following analytical data.

MASS (EI$^+$, m/e (%)): 200(M$^+$, 19), 182(14), 156(40), 111(100). $^1$H NMR (DMSO-d$_6$, δ ppm): 1.69-1.75 (m, 4H), 2.51 (t, J=7.84 Hz, 4H), 3.42-3.48 (m, 4H), 4.51 (t, J=5.00 Hz, 2H), 7.05 (s, 2H). $^{13}$C NMR (DMSO-d$_6$, δ ppm): 24.6925, 32.5363, 60.3863, 120.2828, 141.3420 (2 each). mp.: 45-46° C.

Example 2

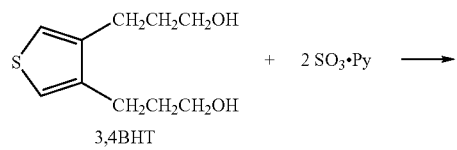

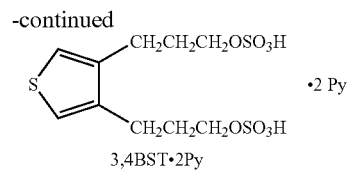

A 50-mL four-neck glass flask was charged with 2.00 g (10.0 mmol) of 3,4-bis(1-hydroxypropyl-3-yl)thiophene (3,4-BHT) and 10 g of N,N-dimethylformamide (DMF). With stirring at 10° C., the flask was further charged with 3.18 g (20.0 mmol) of sulfur trioxide-pyridine complex in several portions. The temperature of the reactant was gradually raised to 20° C. After stirring for 1 hour, the reaction product was analyzed by liquid chromatography. The result of LC gave a new peak, with the peak of 3,4-BHT (as the starting material) disappeared.

The reaction product was concentrated under reduced pressure. The resulting concentrate was dissolved in acetone with heating, and the resulting solution was allowed to stand overnight at 15° C. A gummy solid product separated out. This product was collected by filtration and then dried. Thus, there was obtained 5.01 g of gummy product. This product was identified as 3,4-bis(1-sulfoxypropyl-3-yl)thiophene-dipyridine salt (3,4-BST-2Py) by the following analytical data.

MASS (FAB$^-$, m/e (%)): 359(M$^-$, 19), 279(100), 97(53). $^1$H NMR (DMSO-d$_6$, δ ppm): 1.78 (dt, J$_1$=6.57 Hz, J$_2$=14.21 Hz, 4H), 2.51 (t, J=7.63 Hz, 4H), 3.78 (t, J=6.42 Hz, 4H), 7.06 (s, 2H), 8.10 (dd, J$_1$=6.45 Hz, J$_2$=7.67 Hz, 4H), 8.62-8.66 (m, 2H), 8.94 (d, J=5.19 Hz, 4H). $^{13}$C NMR (DMSO-d$_6$, δ ppm):24.5297, 29.0696, 120.6464, 127.3915, 140.7594, 142.0642 (2 each for above), 146.6423.

Example 3

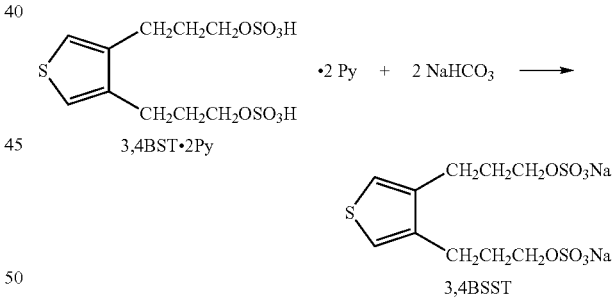

A 50-mL four-neck glass flask was charged with 3.60 g (6.95 mmol) of 3,4-bis(1-sulfoxypropyl-3-yl)thiophene-dipyridine salt (3,4-BST.2Py) and 18 g of N,N-dimethylformamide (DMF). With stirring at 20° C., the flask was further charged with 2.02 g (24.0 mmol) of sodium hydrogen carbonate, and stirring was continued for 30 minutes. The reaction product was concentrated under reduced pressure. The resulting residue was dissolved in 50 g of methanol and the solution was heated at 50° C. A solid product separated out. This solid product was cooled with ice and then filtered with the help of Celite. Upon concentration and drying, the filtrate gave 6.7 g of crude solids. This crude product was dissolved again in methanol. The resulting solution became a gel upon concentration. The gel was dissolved in 20 g of ethanol, and the resulting solution was heated at 50° C. and then cooled with ice. After filtration, washing with ethanol, and drying, there was obtained 2.29 g of white crystals (in a 82.2% yield). The result of LC gave a single peak. This product was identified as 3,4-bis(1-sodium sulfoxypropyl-3-yl)thiophene (3,4-BSST) by the following analytical data.

MASS (FAB$^-$, m/e (%)): 403([M-H]$^-$, 3), 381(100), 359 (9), 279(25), 97(53). $^1$H NMR (DMSO-d$_6$, δ ppm): 1.79 (t, J=7.64 Hz, 4H), 2.48-2.51 (m, 4H), 3.75 (t, J=6.57 Hz, 4H), 7.09 (s, 2H). $^{13}$C NMR (DMSO-d$_6$, δ ppm): 24.5069, 29.0774, 65.1374, 120.6161, 140.7825 (2 each for above). mp.: 215-216° C.

As mentioned above, the present invention provides a new monomer capable of oxidative polymerization to give a useful π-conjugated conducting polymer.

The invention claimed is:

1. 3,4-bis(1-sulfoxyalkyl)thiophene represented by formula 1 below:

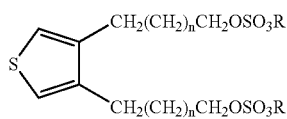

where R denotes a hydrogen atom, alkali metal atom, or alkaline earth metal atom, and n denotes an integer of 1 to 3.

2. 3,4-bis(1-sulfoxypropyl-3-yl)thiophene represented by formula 3 below:

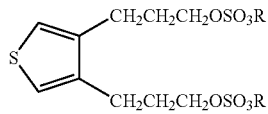

where R denotes a hydrogen atom, alkali metal atom, or alkaline earth metal atom.

3. Sulfoxyalkylthiophene as defined in claim 1 wherein the alkali metal atom is sodium or potassium.

4. Sulfoxyalkylthiophene as defined in claim 2 wherein the alkali metal atom is sodium or potassium.

5. A process which comprises steps of reacting 3,4-bis(1-hydroxyalkyl)thiophene represented by formula 2 below:

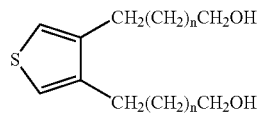

where n denotes an integer of 1 to 3;

with a sulfur trioxide compound to give 3,4-bis(1-sulfoxyalkyl)thiophene represented by formula 5 below:

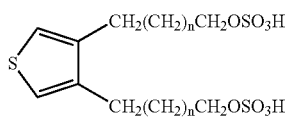

where n is defined as above;

and reacting it with an alkali metal compound or alkaline earth metal compound to give a metal salt of 3,4-bis(1-sulfoxyalkyl)thiophene represented by formula 6 below:

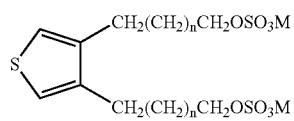

where M denotes alkali metal atom or alkaline earth metal atom and n is defined as above.

6. The process for producing a metal salt of sulfoxyalkylthiophene as defined in claim 5, wherein the alkali metal atom is sodium or potassium.

7. The process for producing a metal salt of sulfoxyalkylthiophene as defined in claim 5, wherein the sulfur trioxide compound is sulfur trioxide, sulfur trioxide-1,4-dioxane complex, sulfur trioxide-DMF (N,N-dimethylformamide) complex, or sulfur trioxide-pyridine complex.

* * * * *